(12) United States Patent
Sender et al.

(10) Patent No.: US 11,938,257 B1
(45) Date of Patent: Mar. 26, 2024

(54) BLOOD-GAS EXCHANGE DEVICE AND METHODS OF USE

(71) Applicant: Inspira-Technologies OXY B.H.N. LTD., Ra'anana (IL)

(72) Inventors: Aviran Sender, Haifa (IL); Angelina Rizansky Rozentsveig, Tel aviv (IL)

(73) Assignee: Inspira-Technologies OXY B.H.N. LTD., Ra'anana (IL)

( * ) Notice: Subject to any disclaimer, the term of this patent is extended or adjusted under 35 U.S.C. 154(b) by 0 days.

(21) Appl. No.: 18/235,515

(22) Filed: Aug. 18, 2023

(51) Int. Cl.
*A61M 1/32* (2006.01)
*A61M 1/14* (2006.01)
*A61M 1/16* (2006.01)
*A61M 1/26* (2006.01)

(52) U.S. Cl.
CPC ............... *A61M 1/32* (2013.01); *A61M 1/14* (2013.01); *A61M 1/1698* (2013.01); *A61M 1/262* (2014.02)

(58) Field of Classification Search
CPC ...... A61M 1/14; A61M 1/1698; A61M 1/262; A61M 1/15–159; A61M 1/1657; A61M 1/3401; A61M 1/3622–3623
See application file for complete search history.

(56) References Cited

U.S. PATENT DOCUMENTS

| | | | | | |
|---|---|---|---|---|---|
| 3,211,148 | A | * | 10/1965 | Galajda, Jr. | ......... A61M 1/3623 261/92 |
| 5,626,819 | A | * | 5/1997 | Novello | .................. A61M 1/32 261/92 |
| 6,454,999 | B1 | * | 9/2002 | Farhangnia | ........... F28F 21/062 604/6.14 |
| 2007/0020142 | A1 | * | 1/2007 | Federspiel | ............. B01D 63/02 604/6.14 |

* cited by examiner

*Primary Examiner* — Benjamin J Klein
(74) *Attorney, Agent, or Firm* — Maxwell L. Minch; Maxwell L Minch Esq. PA

(57) ABSTRACT

The present invention presents a novel oxygenator of the invention provides a revolutionary engineering design and management of the flow regime in a completely different way from the existing and accepted regime in the field of oxygenators, that further lower the risk levels associated with the use of oxygenators and reduces the manufacturing cost. The revolutionary technology is aimed to divert the world of blood oxygenation from the use of technology that relies on a fiber membrane or gas bubbles and causes substantial damage to the patient's blood, towards the use of technology that allows the exchange of gases without a membrane at all and is aimed to reduces risks and improves patient outcome.

16 Claims, 12 Drawing Sheets

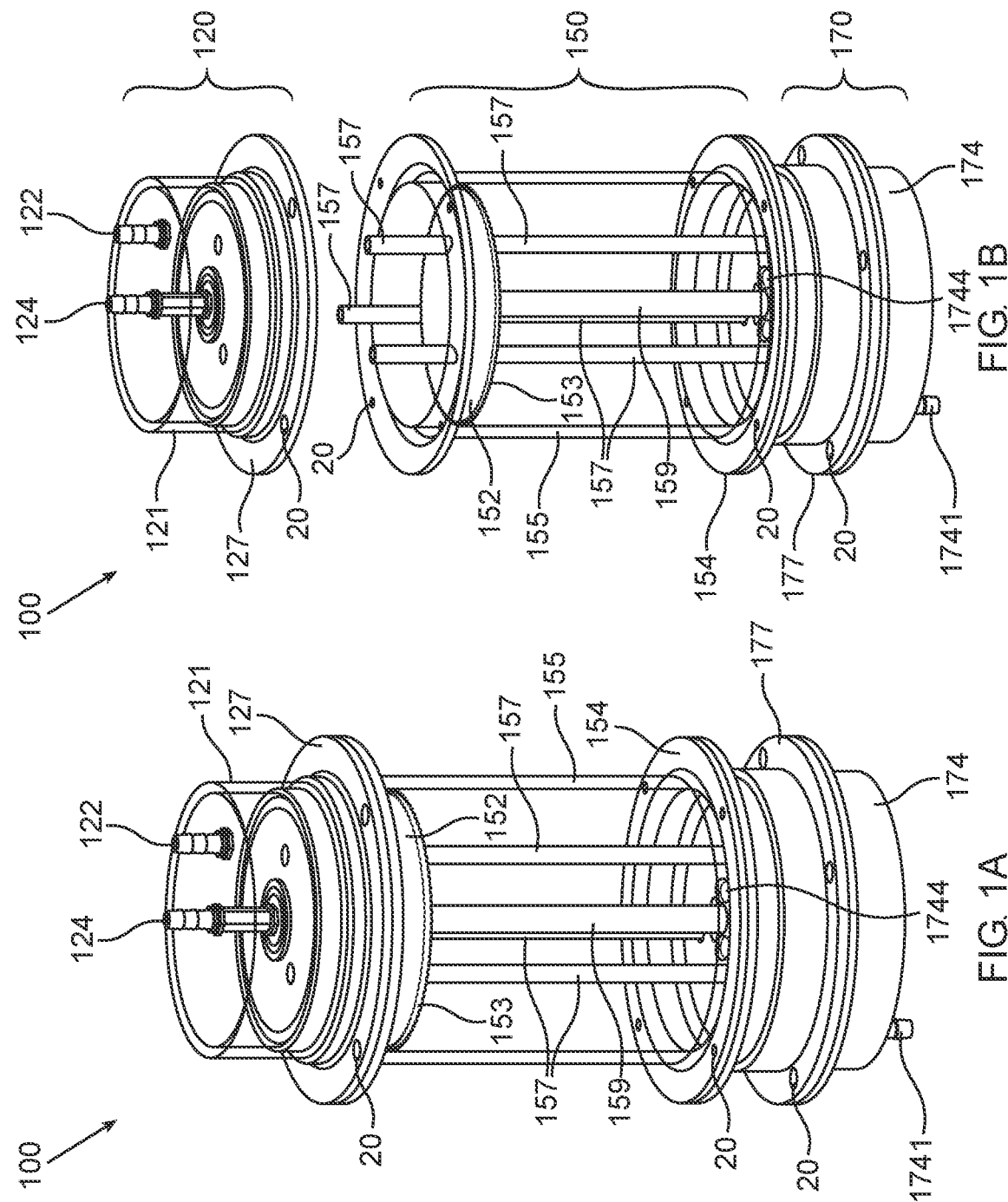

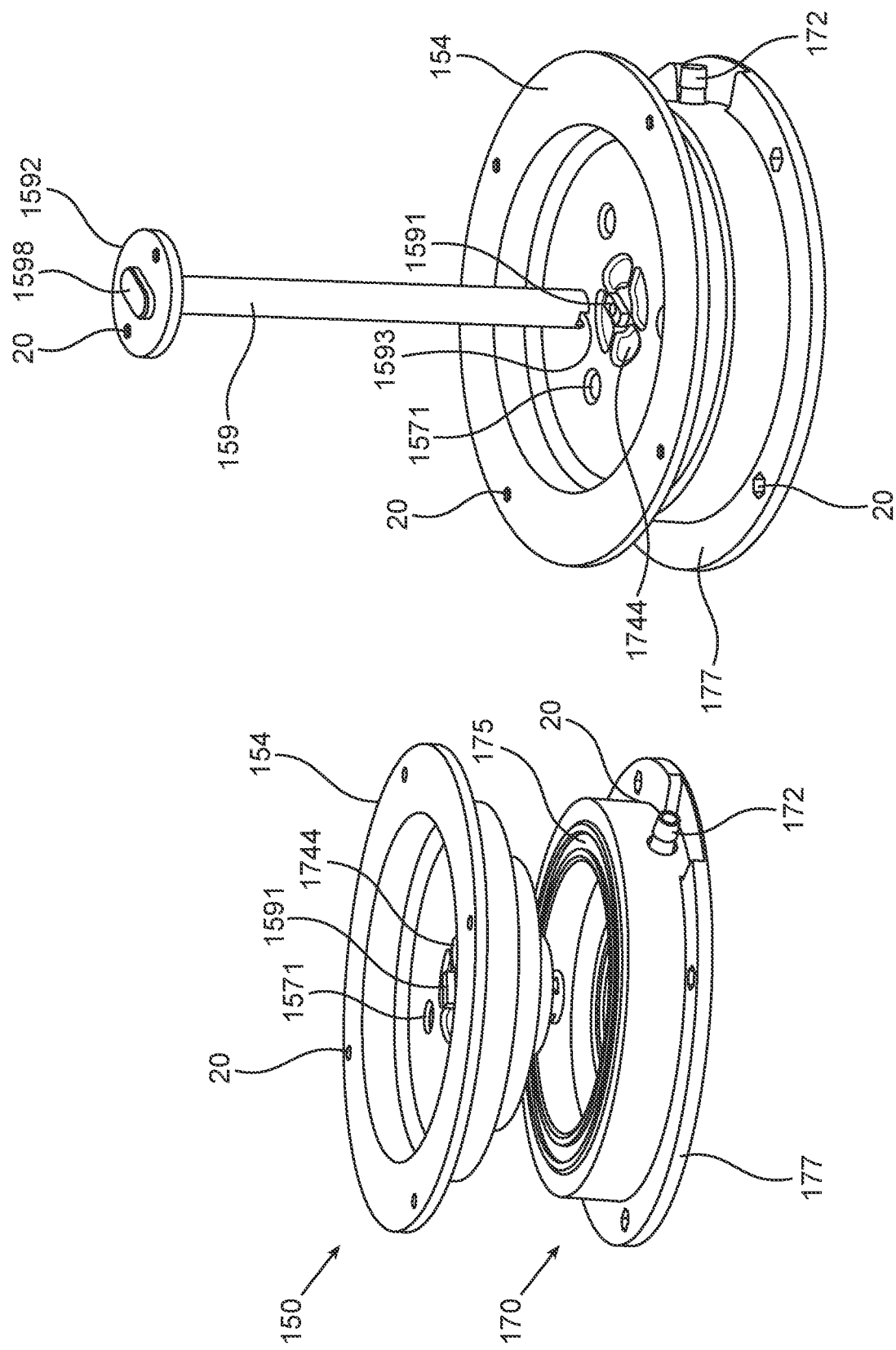

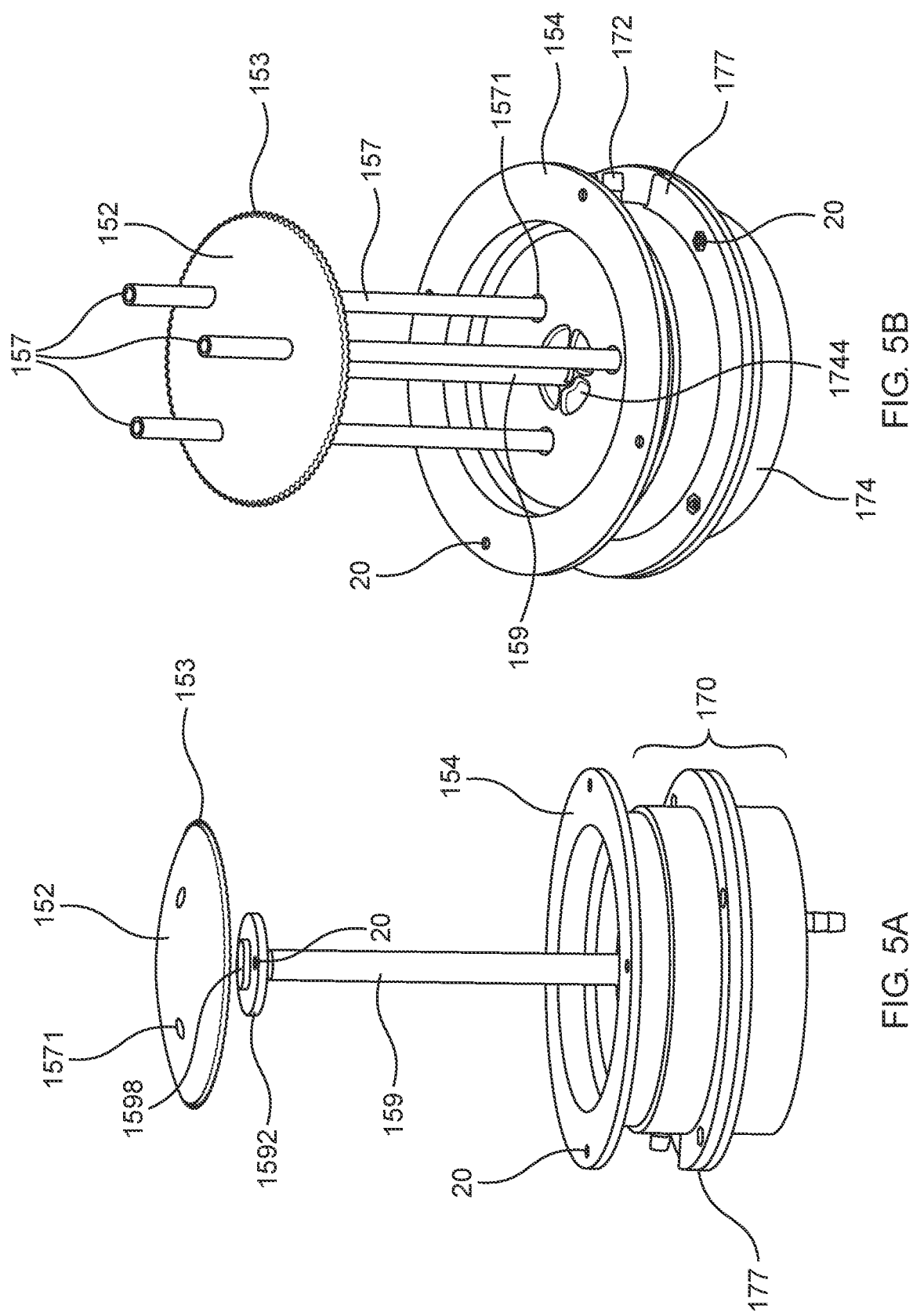

BLOOD-GAS EXCHANGE DEVICE AND METHODS OF USE

FIELD OF THE INVENTION

This invention is directed to a novel liquid-gas exchange device. More particularly, this invention is aimed to provide a revolutionary oxygenator for extracorporeal oxygenation procedures that allows the exchange of gases from the blood without a fiber-based membrane as used in common practice.

BACKGROUND OF THE INVENTION

The world of liquid-gas exchange devices is based today entirely on membrane technology made of hollow fibers. This technology replaced former generation of bubble oxygenators (see for example, ZA80159) that had a direct contact between the blood and the gas, however, the patient's blood was oxygenated by gas bubbles that later revealed as damaging the blood components. For the purposes of this invention the terms "Liquid-gas exchange device", "blood-gas exchange device" and "oxygenator" are all directed to the same and describe a device for exchanging at least one gas between a liquid medium and a gas phase, for example exchange of oxygen and/or carbon dioxide in the blood and may be used hereinbelow interchangeably.

For simplicity of explanation, the term "Blood" as used herein includes whole blood, blood components, plasma, and serum.

The hollow fibers oxygenators have significant limitations due to the material from which the oxygenator is made, the structure of the oxygenator and the blood flow regime. Unlike the natural laminar blood flow in blood vessels inside the body, in existing oxygenators the blood is "forced" to flow in a harmful turbulent flow through many layers of fibers, while experiencing friction and shear forces with the fiber walls. Since the fiber fabric is a significant resistor to blood flow, high pressure differences are formed between oxygenator blood inlet and blood outlet (pressure drop). The existing flow regime, i.e., the unnatural turbulent flow, the high shear forces and the high pressure differences, causes significant damage to the various blood components, including, high hemolysis (breakdown of red cells), damage to white blood cells, activation of the inflammatory system in the body, activation of the immune system, and especially significant damage to the blood dotting system (for more details see: Zangrillo et al., A meta-analysis of complications and mortality of extracorporeal membrane oxygenation, Critical Care and Resuscitation, Volume 15, Number 3, September 2013; F. De Somer, Does contemporary oxygenator design influence haemolysis?, Perfusion 28(4) 280-285, 2013; Paparella et al., Coagulation disorders of cardiopulmonary bypass: a review, Intensive Care Med 30: 1873-1881, 2004.)

The substantial damage to blood components and the hemostasis (i.e., imbalance of the coagulation system), requires the administration of systemic anticoagulants to the patient and constant monitoring in order to prevent the accumulation of blood clots (both in the system and in the patient), neurological hemorrhages, damage to vital organs, an acute inflammatory reaction that damages vital organs and more. In recent years, many efforts have been made to develop membranes made of various materials that will enable efficient gas exchange and cause less damage, but until this moment there is no commercial oxygenator that allows the exchange of gases without a fiber-based membrane, in a way that will reduce membrane-related damages.

The novel blood-gas exchange device provided herein enables efficient gas exchange, without the need for a separating membrane and with direct contact between blood and gas. As such, the oxygenator of this invention is configured to allow liquid (blood or another body fluid) and gas to flow simultaneously within a single chamber that rotates. The rotation movement, together with the unique structure, provides a large surface area for contact between the various mediums and prolongs the time in which the blood comes into contact with the gas in order to optimize the gas exchange. The unique structure and different flow method has the potential to reduce trauma to the blood and subsequently reduce the clinical complications derived from it.

Additionally, as the novel oxygenator provided herein does not use hollow fibers, it eliminates dependence on a single supplier in the world and significantly reduces the production costs of the device.

Thus, there is a need in the art for innovative new technology for oxygenators. The present invention is aimed to provide the next generation of oxygenators. The novel oxygenator of the invention provides a revolutionary engineering design and management of the flow regime in a completely different way from the existing and accepted regime in the field of oxygenators, that further lower the risk levels associated with the use of oxygenators and reduces the manufacturing cost.

SUMMARY OF THE INVENTION

In one main aspect, the present invention is directed to a revolutionary technology that is aimed to divert the world of blood oxygenation from the use of technology that relies on a fiber membrane or gas bubbles and causes substantial damage to the patient's blood, towards the use of technology that allows the exchange of gases without a membrane at all and is aimed to reduces risks and improves patient outcome. The unique properties of the novel blood-gas exchange device as will be described hereinbelow enables more efficient gas exchange and significantly reduces the damage caused to blood components during the gas exchange process, damage that leads to critical clinical complications such as, but not limited to hemolysis, inflammation, blood clots and more.

In one main aspect, the present invention is aimed to provide a novel blood-gas exchange device comprising: a first chamber comprising at least: a gas inlet and a blood inlet for insertion of blood and gas into the blood-gas exchange device for oxygenating the blood and/or for removing carbon dioxide from the blood; a second chamber comprising at least: a blood exit for delivering the oxygenated and/or decarbonated blood out from the blood-gas exchange device, and a gas exit configured to allow flow of gases out from the blood-gas exchange device into the surrounding; and a rotatable chamber connected to said first and second chambers, said rotatable chamber comprising at least: a blood channeling element configured to direct the inserted blood to flow on the walls of the rotatable chamber through at least one set of opening and/or semi-openings; at least one gas opening configured to allow flow of the inserted gas from said first chamber into said rotatable chamber toward the flowing blood, and at least one gas opening configure to allow gas flow from the rotatable chamber to the second chamber; and a motor configured to spin said rotatable chamber; wherein, the circular movement of the rotatable chamber channels the blood to flow along the rotatable chamber walls, forming a blood layer on the wall that directly contacts with the gas and allows gas exchange.

The blood may be inserted into the blood-gas exchange device from a patient in need and returned to the patient upon oxygenation and/or removal of carbon dioxide. Alternatively, the blood may be inserted into the blood-gas exchange device from a blood storage container and returned to a patient in need after oxygenation and/or removal of carbon dioxide.

In some optional embodiments, the gas inlet and gas exit are both positioned in one chamber. In such an embodiment, the at least one gas opening configured to allow gas flow into and from the rotatable chamber is comprised in the chamber that comprise the gas inlet and the gas exit, so as to allow the gas to flow between the two chambers.

In accordance with embodiments of the invention, the formed blood layer is either one of a blood channel or a blood film formed by the division of the inserted blood by the blood channeling element into plurality of smaller portions and the circular movement of the rotatable chamber.

Optionally, the blood channeling element is a dome like surface having at least one set of openings or semi-openings at its circumference. Alternatively, the blood may be divided into small tube elements at the exit from the blood inlet connector and spread over the wall 155 with one or more thin tubes. Alternatively, the inserted blood may be divided into small shares following tubing placement at the exit point of the blood inlet connector in a manner that ensures that the blood is directed and distributed over the rotatable chamber wall.

In some embodiments of the invention, the at least one set of openings or semi openings of the blood channeling element, is adjacent to the rotatable chamber wall such that the blood that flows through the set of openings or semi-openings is forced to flow downward on said wall until it reaches the second chamber. Optionally, the blood channeling element comprises at least two sets of openings/semi openings, each set of opening is adjacent to a wall such that the inserted blood flows within the rotatable chamber on each of said adjacent walls until it reaches the second chamber.

In some optional embodiments, the gas opening is configured to insert into the blood-gas exchange device gas or a mixture of gases such as, but not limited to pure oxygen, air, enriched air with oxygen at various ratios, nitrogen, carbon dioxide and others.

Optionally, the blood-gas exchange device of the invention further comprises at least one perforated gas column configured to connect between one gas opening at the first chamber and one gas opening at the second chamber, said at least one perforated gas column is crossing through said rotatable chamber and allows flow of gas from the column toward the flowing blood and vice versa.

Preferably but not necessarily, gas exchange that occurs within the blood-gas exchange device provided herein is either oxygenation of the blood or decarbonation of the blood or a combination thereof.

The blood-gas exchange device provided herein allows the dwell time for gas exchange to be elongated by the circular movement of the rotatable chamber.

In some embodiments, the blood inlet and blood exit, each may be connected to a tube that delivers blood from the patient in need and/or a storage container into the blood-gas exchange device and return the blood following the gas exchange to the patient in need. Yet, in further optional embodiments, the blood-gas exchange device of the invention may further comprise at least one pump configured to withdraw blood from the patient in need or from the storage container into the blood-gas exchange device and to transfer the oxygenated/decarbonated blood back to the patient in need.

In accordance with embodiments of the invention, the flow of gas through the gas inlet and exit of gas through the gas exit allows a gradient flow of gases within the blood-gas exchange device that enables gases from the blood to diffuse into the rotatable chamber and gases from the rotatable chamber to diffuse into the flowing blood.

The blood-gas exchange device of the invention may be used for various systems and procedures including without limitation extracorporeal life support systems (the device may be used during procedures such as ECMO and cardiopulmonary bypass), intravascular oxygenation systems, and implanted oxygenating and/or gas exchanging devices.

The blood-gas exchange device of the invention may be used mutatis mutandis with other liquids, for example instead of blood another body fluid may be inserted for gas exchange procedure.

BRIEF DESCRIPTION OF THE DRAWINGS

Examples illustrative of embodiments of the disclosure are described below with reference to figures attached hereto. Dimensions of components and features shown in the figures are generally chosen for convenience and clarity of presentation and are not necessarily shown to scale. Many of the figures presented are in the form of schematic illustrations and, as such, certain elements may be drawn greatly simplified or not-to-scale, for illustrative clarity. The figures are not intended to be production drawings.

The figures (FIGS.) are listed below.

FIG. 1A is a schematic isometric view of a novel oxygenator according to one optional embodiment of the invention. This drawing depicts the oxygenator upper, middle and lower compartments assembled to each other.

FIG. 1B depicts the oxygenator of FIG. 1A in a partial exploding view showing the upper compartment separated from the middle and lower compartments.

FIG. 4A is a schematic isometric view illustration showing the "base" of the bottom chamber and the "floor" of the middle chamber partially separated from each other to demonstrate the manner they are assembled one onto the other.

FIG. 4B is a schematic isometric view illustration showing the "base" of the bottom chamber and the "floor" of the middle chamber of FIG. 4A connected, and a rotation rod that connects between the dome of the middle chamber to the floor of the middle chamber which connects to the engine and operates as the main rotation axis.

FIGS. 5A-5C are schematic sequential illustrations showing the assembly of the components of the middle unit on top of the base of the middle unit and the bottom unit of the oxygenator of the invention, wherein, FIG. 5A is an isometric side view illustration of the assembly of the dome; FIG. 5B is an isometric top view illustration of the assembly of the perforated gas tubes; and FIG. 5C is the isometric top view illustration shown in FIG. 5B further showing partial assembly of middle chamber housing.

DETAILED DESCRIPTION OF EMBODIMENTS OF THE INVENTION

Figure 2A:
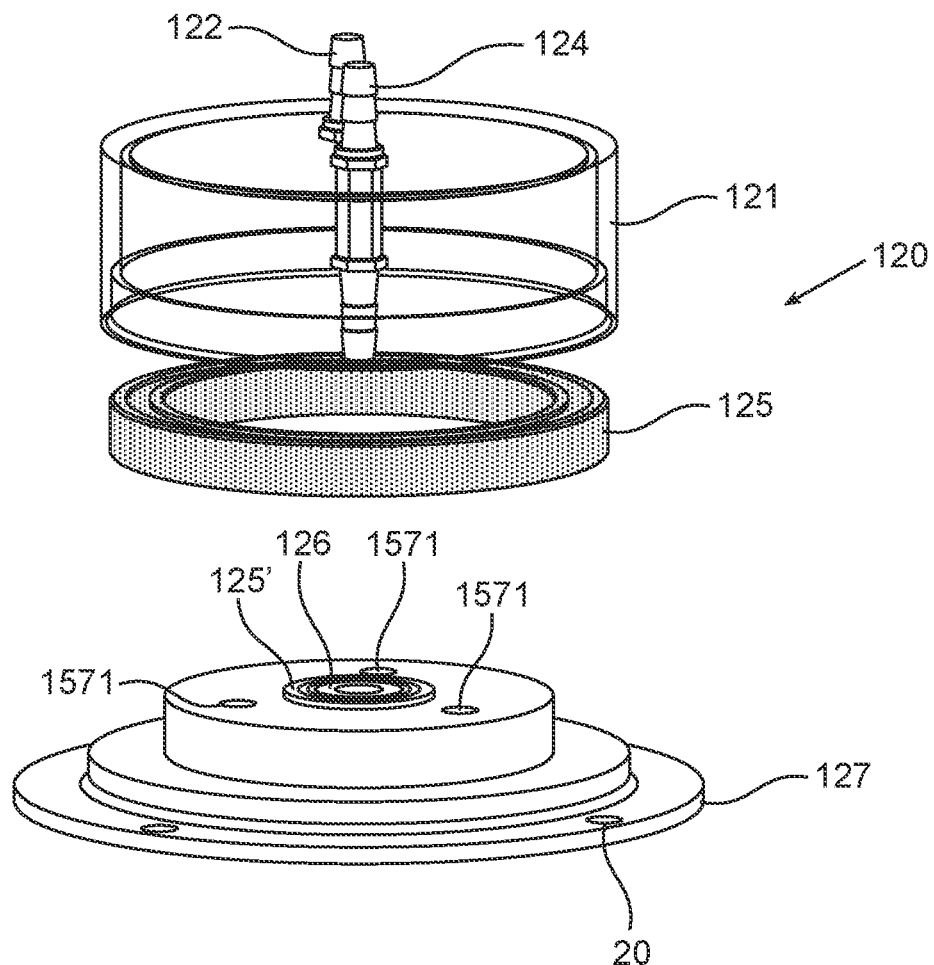
FIGS. 2A-2B are schematic partial exploding view and isometric view illustrations respectively, of the upper chamber of the oxygenator illustrated in FIGS. 1A-1B.

In the following description, various aspects of the novel blood-gas exchange device of the invention will be described. For the purpose of explanation, specific configurations and details are set forth in order to provide a thorough understanding of the invention.

Although various features of the disclosure may be described in the context of a single embodiment, the features may also be provided separately or in any suitable combination. Conversely, although the disclosure may be described herein in the context of separate embodiments for clarity, the disclosure may also be implemented in a single embodiment. Furthermore, it should be understood that the disclosure can be carried out or practiced in various ways, and that the disclosure can be implemented in embodiments other than the exemplary ones described herein below. The descriptions, examples and materials presented in the description, as well as in the claims, should not be construed as limiting, but rather as illustrative. The oxygenator provided herein may be used as part of an extracorporeal oxygenation system and may be used in operating rooms and intensive care units in hospitals. The oxygenator allows efficient and safe gas exchange without the membrane present in commercial oxygenators available in the market.

In accordance with one embodiment of the invention the oxygenator is a disposable device, designed to be used in a single patient. The components that are in direct contact with the patient's blood are manufactured from biocompatible materials., i.e., from materials approved for direct contact with blood, such as but not limited to stainless steel and polycarbonate. All components are preferably coated with anti-coagulation materials to enable long-term operation.

The oxygenator may be designed to fit with high flow extracorporeal oxygenation systems or low flow extracorporeal oxygenation systems as described by the applicant in PCT/IL2021/051431. Additionally, the oxygenator provided herein can fit both short term operations (such as Cardiopulmonary Bypass (CPB)), and long duration operation (such as Extracorporeal Membrane Oxygenation (ECMO)).

Reference is now made to the drawings:

FIG. 1A is a schematic isometric view of novel oxygenator 100, and FIG. 1B depicts the oxygenator of FIG. 1A in a partial exploding view with the upper chamber separated from the middle and lower chambers. Oxygenator 100 preferably comprise three main chambers: first chamber 120, a second chamber 170, and a rotatable chamber 150. The first and second chambers that comprise inlets and outlets of blood and gas are conceptually stationary chambers, however it should be clear that the above separation to 3 chambers is only made for simplicity of explanation, and one part that served as a base of one chamber is also the "ceiling" of the adjacent chamber, and although most of the components of the first and second chambers are stationary, some of the components are rotatable together with the central rotatable chamber as will be described in detail with reference to the drawings hereinbelow. Also, it should be clear that other optional embodiments of the invention are possible and should be considered within the scope of this invention, as long as the inlet and outlet connectors of blood and gas into and out of the oxygenator are stationary and the chamber in which the oxygenation process occurs is rotatable.

Gas, preferably pure oxygen, or air, or enriched air with oxygen (or any other desired gas according to the use) and blood from a patient's body are inserted into oxygenator 100 through dedicated tubes configured to fit with connectors 122, 124. The gas is inserted into first chamber 120 of oxygenator 100. The blood from the patient's body is crossing through the first chamber through connector 124 and is being spilled onto blood channeling element 152. In the specific example illustrated herein, the blood channeling element is a dome like structure with holes/semi-holes/notches/slits 153 positioned along its circumference in a manner that allows the blood to flow downward toward second chamber 170 only through the inner surface (inner wall) 155 of rotatable chamber 150. The rotation movement of chamber 150 is aimed to increase the flow duration of the deoxygenated blood, and thus to increase the gas exchange duration to allow substantive oxygenation of the flowing blood, until the blood reaches second chamber 170 of oxygenator 100 and being collected into a dedicated chamber 174, having a connector 1741 that is further connected to a suitable tube that return the blood back into the patient's body.

Second chamber 170 besides collecting the blood, also allows release of the gases accumulated in the rotatable chamber inner space, out into the surrounding by a dedicated exit connector (not shown in these views) comprised in base 177, such that excess of oxygen ($O_2$) that has not been exchanged together with carbon dioxide ($CO_2$) that was exchanged from the patient's blood into the oxygenator inner space, are being discharged out from the oxygenator into the surrounding, and the oxygenated blood is being collected in a blood collection container 174 and delivered back to the patient's body through a tube connected to the blood exit connector 1741 of bottom chamber 170 as mentioned above.

If other gases were used in the gas exchange procedure, then the mixture of gases that accumulated within the oxygenator are released to the surrounding.

In some optional embodiments, the gas exit connector is comprised in the first chamber or in the rotatable chamber, while the same concept applies to the manner the residual gas is released from the oxygenator.

FIG. 1B provides a view of the upper portion of rotatable chamber 150. In this view, dome 152 that channels the patient's blood to flow on the circumference of the rotatable chamber cover 155 (inner wall) is shown. Also shown are three perforated gas columns 157 that receive the gas from inlet 122 and configured to allow diffusion of gas from the holes comprised in the perforated gas column toward the deoxygenated blood that circulates on cover 155 inner wall. Also shown in this view is rotation rod 159 that is aimed to hold the blood channeling element 152 is its position, housing 121 of first chamber 120, ceiling 127 and floor 154 of rotatable chamber 150, drainage holes 1744 that allow drainage of the oxygenated blood from the middle rotatable chamber to the second chamber, and holes 20 for screws to allow connecting the various parts of oxygenator 100 to each other.

Yet, in some further embodiments the gas flow through the gas openings from directly from first chamber into the rotatable chamber without entering into perforated columns. Detailed description of each chamber and its major components will be described hereinbelow.

Figure 2B:
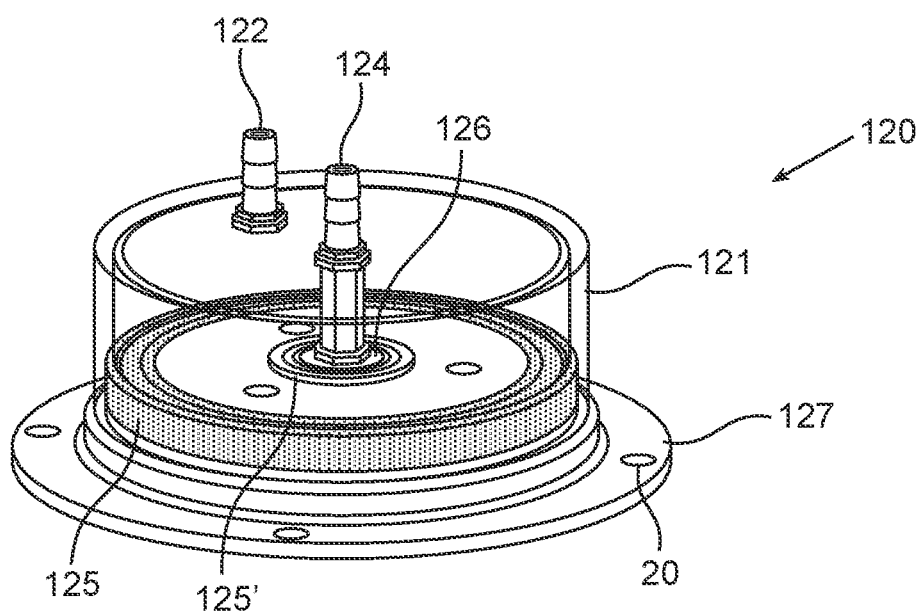

FIGS. 2A-2B are schematic partial exploding view and isometric view illustrations respectively, of first chamber 120 of oxygenator 100 illustrated in FIGS. 1A-1B according to one optional embodiment of the invention. First chamber 120 comprised a main bearing 125 that separates between the fixed stationary portion of oxygenator 100 on top of it, and the rotatable part of oxygenator 100 positioned below it. Bearing 125 is placed on top of base 127 that functions as the ceiling of middle chamber 150 and thus rotates together with rotatable chamber 150. Housing 121 is situated on top of bearing 125 and contains blood inlet connector 124 that is extended toward middle chamber 150 and being held by a dedicated base 126 and a smaller bearing 125'. Housing 121 further comprise a gas inlet connector 122. Gas inlet connector 122 protrudes outward from housing 121, and the gas inserted into first chamber 120 spreads within housing 121, such that the housing on top of bearing 125 functions as a gas container. Ceiling 127 further comprise holes 1571 configured to allow the gas to pass through them into gas columns 157 connected to each hole. It should be clear that the above describes a single optional embodiment of the invention, and the position of the blood and gas inlets may vary. Also, the perforated gas columns are optional and if included, their number and position may also vary.

Optionally, ceiling 127 may comprise additional holes 20 on its circumference to allow connection of the base to additional parts of the oxygenator by screws. Other attachment means known in the art such as but not limited to gluing may also be used.

Figure 2C:
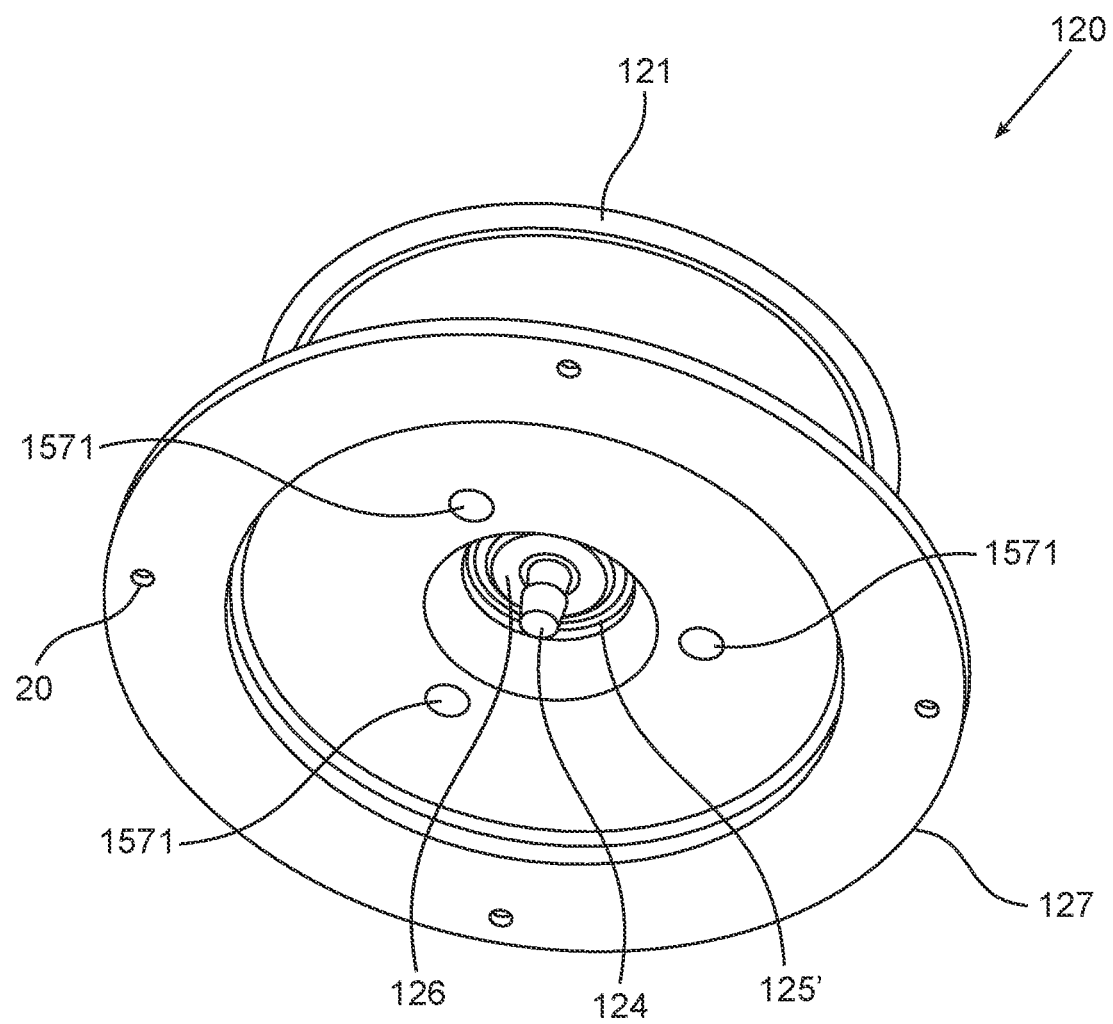
FIG. 2C is a schematic isometric bottom view illustration of the upper chamber of the oxygenator of FIG. 2A.

FIG. 2C is a schematic isometric bottom view illustration of first chamber 120 of oxygenator 100 allowing to view ceiling 127 from the bottom. In this view, the bottom portion of blood inlet connector 124 is shown directing the blood from the patient's body through first chamber 120 into middle rotatable chamber 150, onto the blood channeling element 152 to allow it to flow through the openings at the perimeter of the blood channeling element as will be described hereinbelow with reference to FIG. 6A. Blood inlet connector 124 is being held by base 126 and bearing 125'. Also shown in this view, openings 1571 that allows passage of gas from first chamber 120 into rotatable chamber 150, housing 121, and holes 20 for screws to attach the first chamber to the middle rotatable chamber.

As mentioned above, when oxygenator 100 is operating, the first chamber 120 comprises stationary housing 121 thanks to bearing 125 and 125', while ceiling 127 of chamber 120 rotates such that the blood inserted through blood inlet connector 124 spreads onto the rotating blood channeling element 152 (the dome) and ensures that the inserted blood is directed to the circumference of the dome.

Figure 3A:
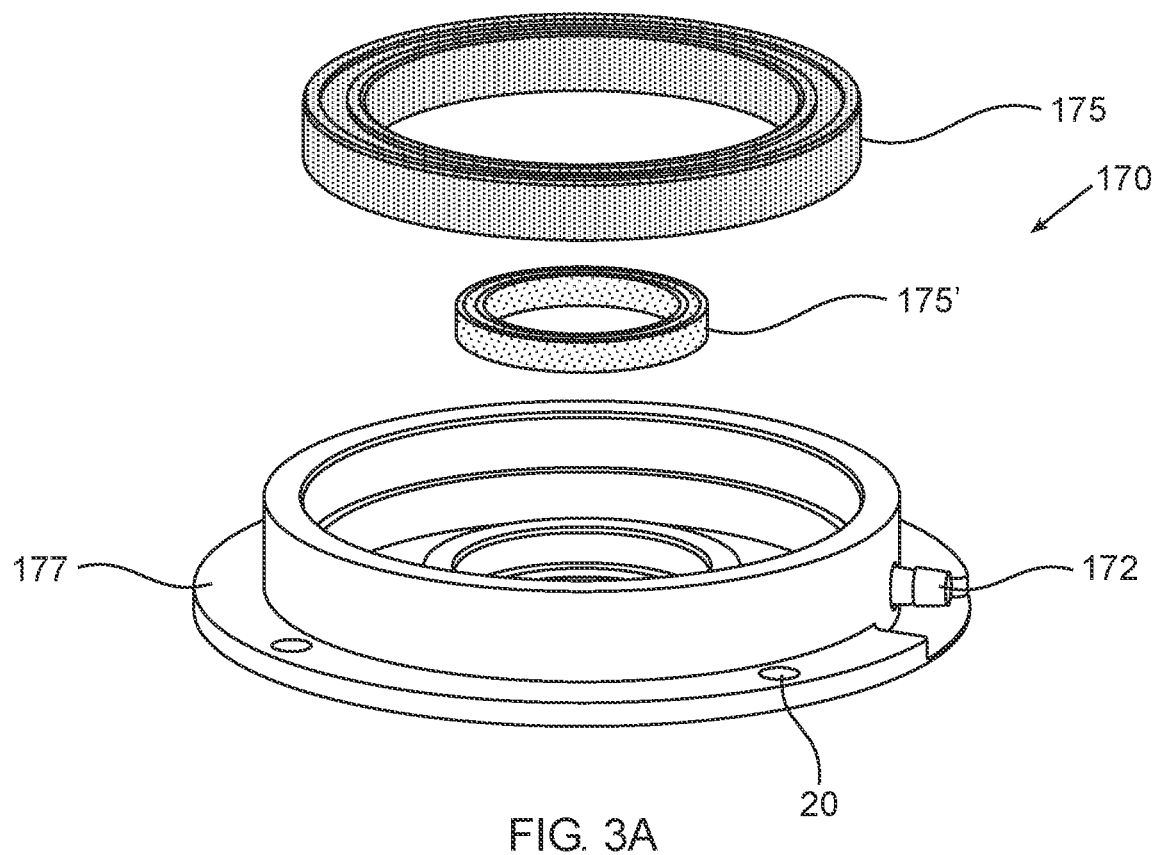
FIGS. 3A-3B are schematic exploded view illustration and isometric top view illustration respectively part of the bottom chamber of the oxygenator of the invention according to some optional embodiments.
Figure 3B:
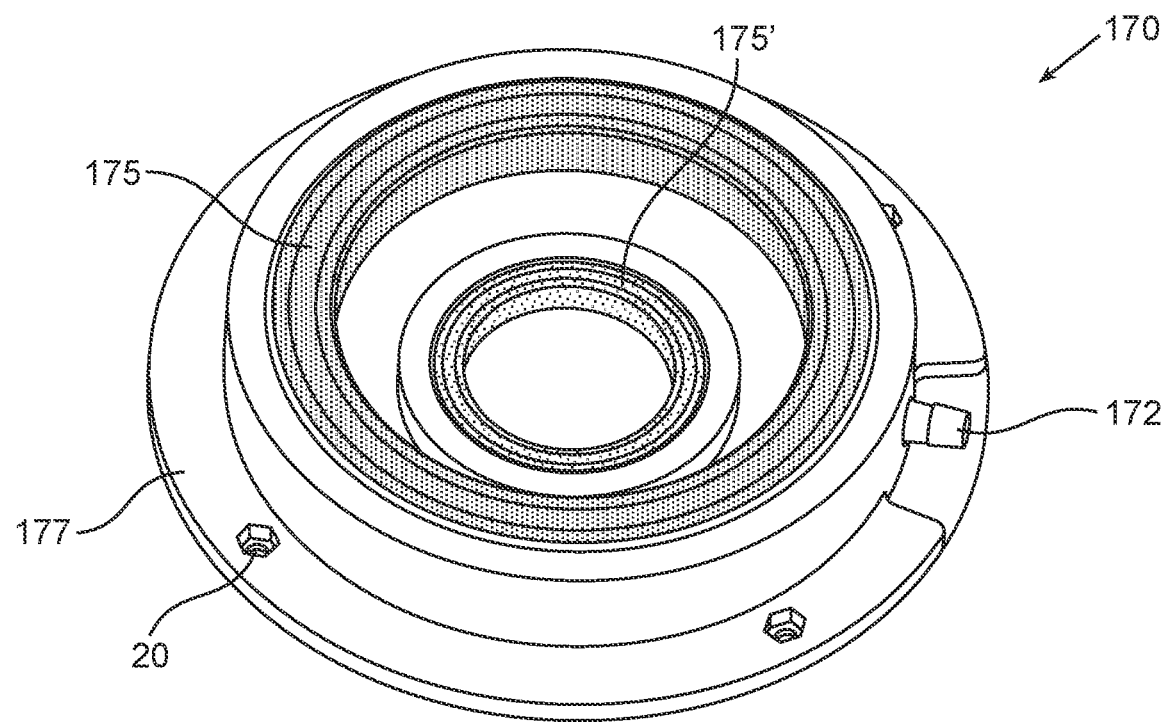

FIGS. 3A-3B are schematic partial exploded view illustration and partial isometric top view illustrations respectively of second chamber 170 according to some optional embodiments. Base 177 comprises a gas exit pipe 172 to allow gases to be released out from oxygenator 100 to the surroundings. Two bearings are mounted on base 177. Large bearing 175 and small bearing 175'. Bearing 175 and small bearing 175' allowed the rotation of rotatable chamber 150 such that the parts positioned on top of it are rotating, while the parts positioned below bearing 175 are stationary. Bearing 175 and small bearing 175' are configured to allow rotation movement to floor 154 that allows the rotation of the middle rotatable chamber 150 while maintaining base 177 to remain stationary. Optionally, base 170 may contain holes 20 that allow to mechanically attach it by screws to other parts of oxygenator 100.

FIG. 4A is a schematic isometric view illustration showing the "base" 177 of second chamber 170 and the "floor" 154 of rotatable chamber 150 partially separated from each other to demonstrate the manner they are assembled one onto the other. Floor 154 is positioned on top of bearing 175 and small bearing 175' thus, it rotates upon usage of oxygenator 100.

FIG. 4B is a schematic isometric view illustration showing the "base" 177 of second chamber 170 and the "floor" 154 of rotatable chamber 150 of FIG. 4A connected, and rotation rod 159 that connects the blood channeling element (the dome in this specific embodiment) of the rotatable chamber to floor 154 which connects to an engine and operates as the main rotation axis. As illustrated in these drawings, floor 154 comprises holes 1571. On top of each hole optionally, a perforated gas column 157 is attached at the rotatable chamber 150 (columns are not shown in this drawing). In this embodiment, the residual gas flows through holes 1571 into second chamber 170 and released to the surrounding through gas exit pipe 172. The number of holes 1571 may be correlated to the number of perforated gas columns 157 or exceed above it and may vary according to various optional designs of the oxygenator.

Floor 154 further comprises at least one drainage hole 1744 that allows drainage of the oxygenated blood from the rotatable chamber 150 to the blood collection chamber 174 to be delivered back to the patient's body through a tube connected to blood exit connector 1741 (shown in FIG. 5A) of second chamber 170. Blood exit connector 1741 may be positioned horizontally, in a slop, or else, and further it may be positioned elsewhere along the blood collecting unit, and the above embodiment should be considered as a non-limiting, exemplifying option.

In the specific embodiment described above, floor 154 further comprises an opening that allow the insertion of a dedicated connector (shown in FIG. 4B) having a protrusion 1591 complementary to a socket 1593 at the bottom tip of rotation rod 159, to allow stable connection of the parts that are further fastened to each other by screws or any other suitable connection means. The upper tip of rotation rod 159 has a plate 1592 that allows to stably connect it to dome 152 by screws or any other attachment means suitable for this purpose. Plate 1592 may be designed in various shapes and may be an integral part of rotation rod 159 or separated thereof, and the design described herein is only one none limiting optional example. Plate 1592 comprise a protruding tip 1598 that is complementary to a niche at the bottom side of blood channeling element 152 (the dome in this specific example) and aimed to further stabilize and nail the rotation rod and the dome. Also shown in these drawings are holes 20 that provide one optional attachment option to connect the parts of oxygenator 100 to each other by screws. If other attachment means are used, these holes may be redundant.

Figure 4C:
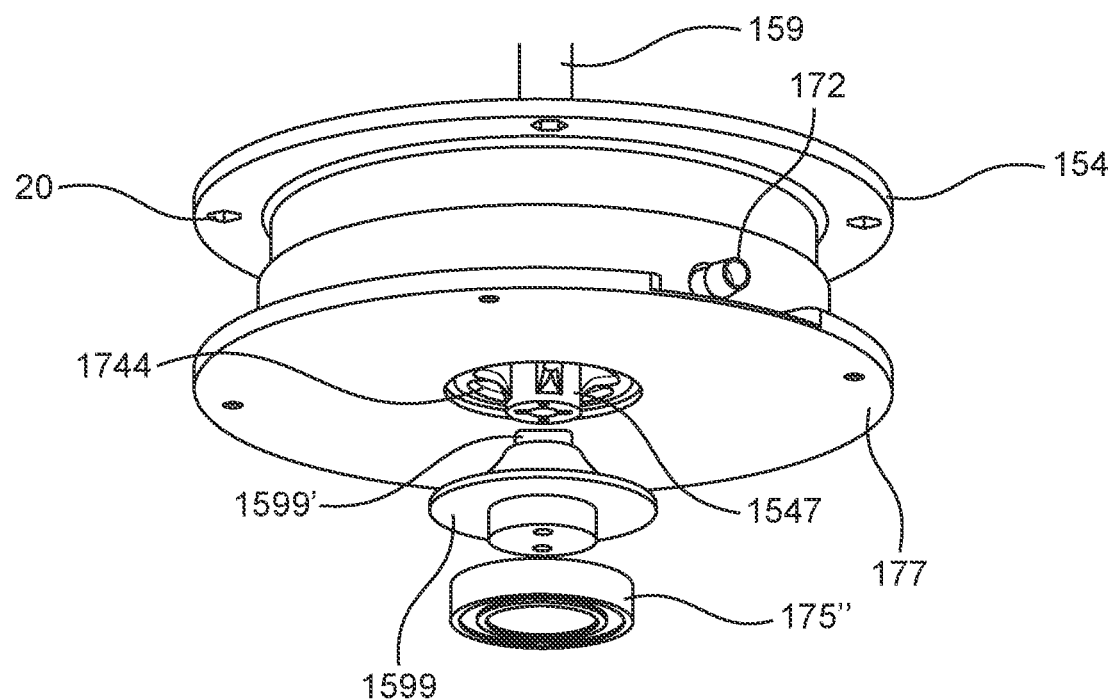
FIG. 4C is a schematic isometric bottom view illustration showing major components of the second chamber and bottom area of the middle rotating chamber of the oxygenator of the invention demonstrating the manner they are assembled to each other according to optional variations of the invention.

FIG. 4C is a schematic isometric bottom view illustration showing major components of the second chamber 170 and bottom area of rotatable chamber 150 of oxygenator 100 demonstrating the manner they are assembled to each other according to optional variations of the invention. In this view, connector 1599 is shown with protrusion 1599' at the top end that is complementary to socket 1547 of rotation floor 154. Connector 1599 is positioned on top of bearing 175" that functionally allow the motor to rotate connector 1599 together with floor 154 and with all the middle rotatable chamber 150, while the base 177 and blood collecting chamber 174 of second chamber 170 remain stationary and connected to a blood tube that returns the oxygenated blood back to the patient's body.

Also shown in this view are blood drainage openings 1744, gas exit pipe 172, and rotatable floor 154 at the bottom end in the connection area to connector 1599.

Figure 4D:
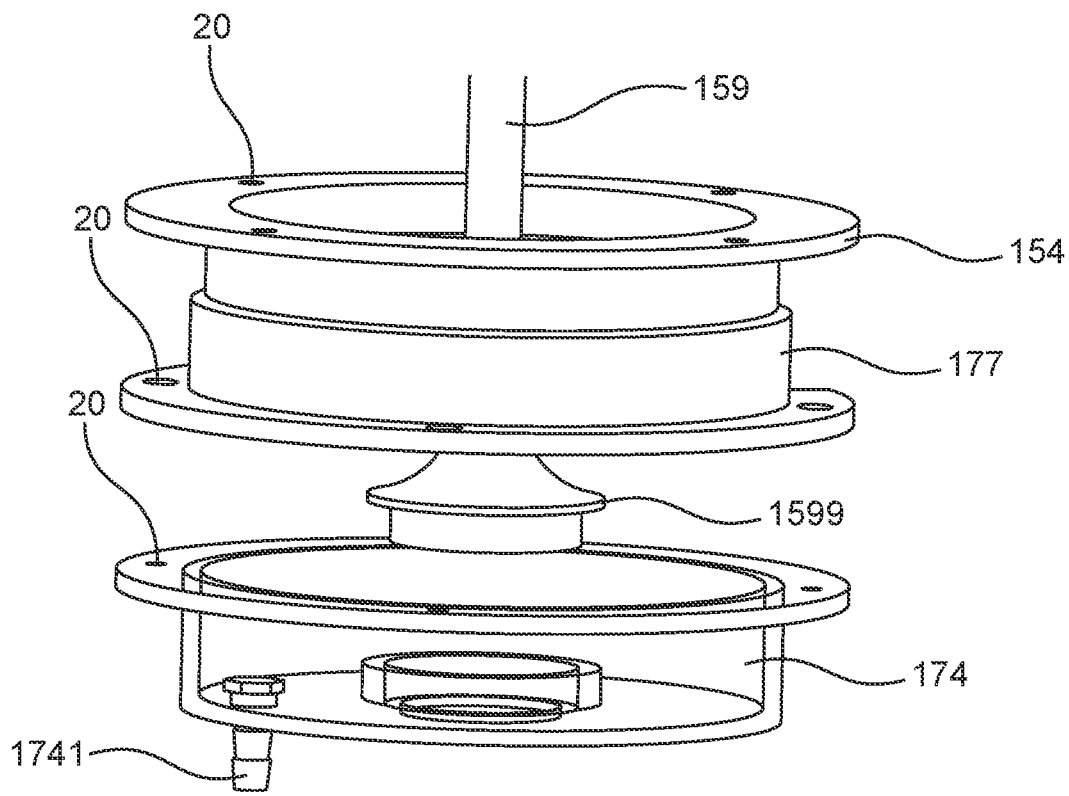
FIG. 4D is a schematic isometric partial exploded side view illustration of the parts illustrated in FIG. 4C with the addition of the blood collecting unit.

FIG. 4D is a schematic partial exploded side view illustration of the oxygenator parts illustrated in FIG. 4C with the addition of the blood collecting unit 174. Shown at this drawing from top to bottom: rotation rod 159, rotating floor 154, base 177, rotating connector 1599, blood collecting chamber 174, blood exit connector 1741 and holes 20.

Figure 5C:
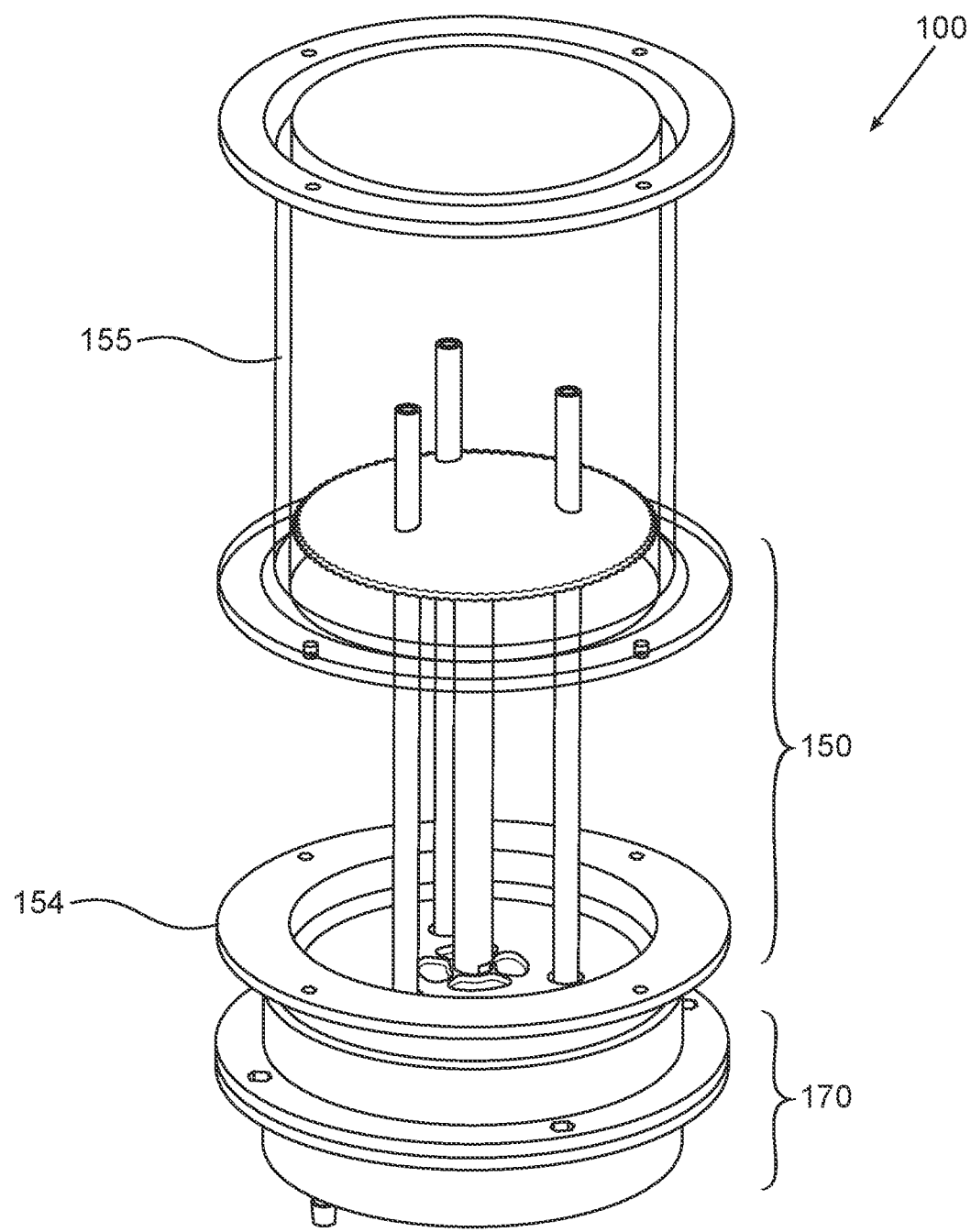

FIGS. 5A-5C are schematic sequential illustrations showing the assembly of the of the middle unit parts on top of the base illustrated in FIG. 4D of the oxygenator of the invention. FIG. 5A is a side isometric view illustration of second chamber 170 of oxygenator 100 connected to floor 154 of rotatable chamber 150 and to rotation rod 159. Optionally, rotation rod comprises a plate 1592 at its upper end that allows to fix it to the blood channeling element 152 (the dome). Plate 1592 may be circular, oval or have any other geometrical shape. It may be an integral part of rotation rod 159 or separated thereof. In some optional embodiments, plate 1592 may comprise a protruding tip 1598 that is complementary in its shape to a complementary notch at the bottom surface of dome 152 to further stabilize and tighten the connection between the two parts and to allow safe rotation of the middle rotatable chamber 150. In other optional connection option, blood channeling element 152 can also connect to any other rotating chamber, for example to ceiling 127, or else.

Also shown in this view, the dome 152 having a perimeter with semi-holes that are aimed to allow the deoxygenated blood to flow downward only through them at the circumference of rotatable chamber 150, and holes 1571 for passage of the gas columns from gas container 121 at the first chamber 120 to rotatable chamber 150 for oxygenating the patient's blood.

FIG. 5B is a top isometric view illustration of the second chamber and rotatable chamber of the oxygenator of the invention without the housing of the rotatable chamber, showing the different layers of the device, according to some optional embodiments of the invention. In this specific example, the second chamber 170 of oxygenator 100 is connected to floor 154 of rotatable chamber 150, and further to other components of rotatable chamber 150. In more details, rotation rod 159 is connected throw floor 154 to base 177 and blood collection unit 174 and further to an engine that allows the rotation of the middle rotatable chamber 150 (not shown in this view). Gas perforated columns 157 are attached to floor 154, optionally by glue at their bottom and pass through dedicated holes 1571 through dome 152 toward the upper chamber and the gas container (not shown in this view). Also shown in this view are semi-holes 153 at the circumference of dome 152, blood drainage openings 1744, and gas release pipe 172. Holes for attachment of various parts of oxygenator 100 to others by screws are also shown.

FIG. 5C is a schematic isometric top view illustration of FIG. 5B further showing assembling of housing 155 onto the floor 154 of rotatable chamber 150 of oxygenator 100. Housing 155 is attached at the bottom to floor 154 and at the top to ceiling 127 (not shown in this view), preferably but not necessarily by screws. Rotatable chamber housing 155 encompassing tightly the dome 152 such that the inner wall of housing 155 contact with the deoxygenated blood that flows into oxygenator 100 through semi-holes 153. Due to gravitation forces the blood flows downward, however, since the middle chamber 150 rotates, the rotation movement shifts the blood flow direction and consequently, the time that the blood circulates along housing 155 until it reaches the blood drainage openings at the bottom (the dwell time) and enters into the blood collection unit extends substantially. During that time, gas from the gas columns 157 flows toward the deoxygenated blood and gas exchange is performed, such that oxygen enters the blood and carbon dioxide is released from the blood. Alternatively, only carbon dioxide is released from the blood. As the time flow duration along the housing inner wall extends, the oxygenation time of the blood extends substantially as well.

Figure 6A:
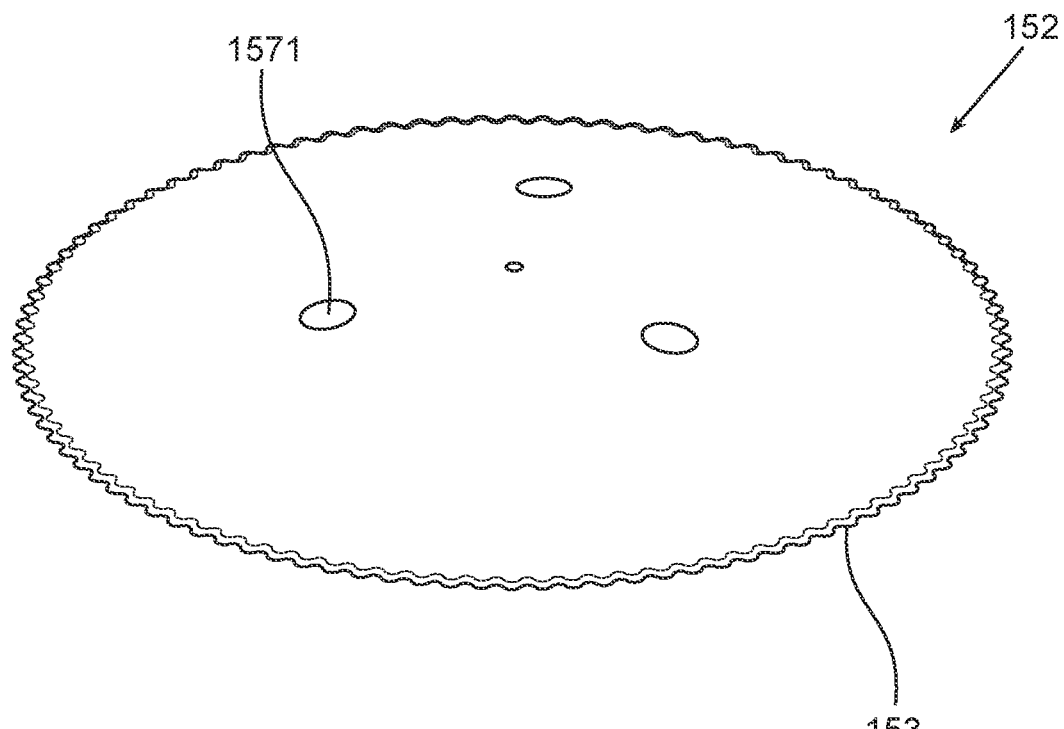
FIG. 6A is a schematic illustration of the middle unit dome according to one optional embodiment.

FIG. 6A is a schematic illustration of dome 152 according to one optional embodiment of the invention. Dome 152 comprises at least one hole 1571 configured to allow passage of at least one gas column through it. In the specific embodiment illustrated in this figure the dome comprises three holes for three gas columns. It should be clear that the number of holes which are correlated with the number of gas columns may vary according to various optional designs. Also shown in this view are semi-holes 153 at the circumference of dome 152.

Figure 6B:
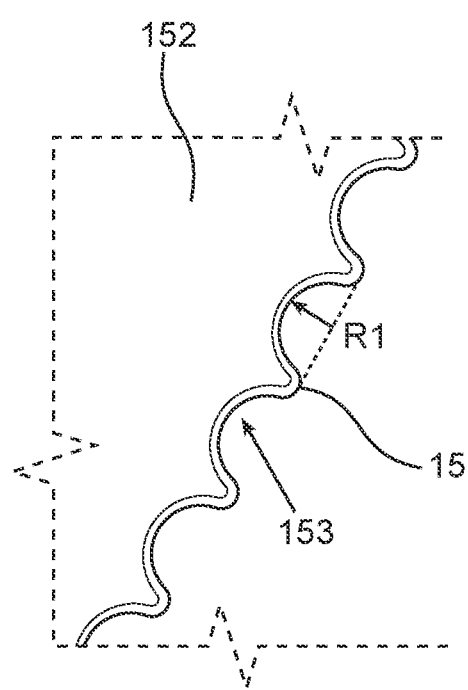
FIGS. 6B-6C are schematic close up views illustrating optional designs of the outer margins of the dome of FIG. 6A.
Figure 6C:
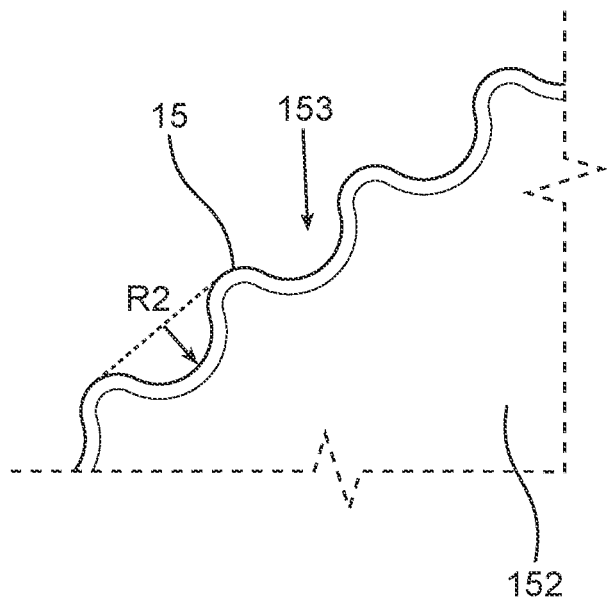

FIGS. 6B-6C are schematic closeup view illustrations of optional designs of semi-holes 153 at the circumference of the dome. The radius of semi holes 153 may vary, and the number of the semi holes changes accordingly. For example, the radius R1 of semi hole 153 in FIG. 6B is smaller than the radius R2 of semi hole 153 of FIG. 6C. Accordingly the number of semi-holes having radius R1 around the circumference of dome 152 in FIG. 6B is higher than the number of semi-holes having radius R2 that is larger than radius R1, assuming that the perimeter length is the same. In addition to differences in the radius, the curvature of the semi holes 153 may vary depending on the desired design. The septum 15 between two adjacent semi-holes may have variety of shapes (e.g., sharp, blunted, rounded) and may have different thickness. In some other optional embodiments instead of semi holes the blood may flow through a continues thin notch at the circumference of dome 152.

As depicted in the figures above, while in the commercially available oxygenators the gas flows inside hollow fibers and has a considerable barrier to diffusion, the novel oxygenator described herein is advantageous over the currently available oxygenator as it enables a direct blood gas contact which is practically diffusion with zero thickness of the barrier for diffusion. Less/No barrier results in better gas diffusion rate, and better gas diffusion rate requires less surface area for gas transfer. In addition, the absence of a membrane within the oxygenator enables less contact with foreign material, thus, less harmful effect on the blood components, less resistance to flow, thus, reduced pressure drops, and consequently, a reduced shear forces (which is dependent on the pressure drop).

Yet, in the novel oxygenator, compared to currently available oxygenators, the blood that enters through the blood inlet and poured onto the blood channeling element that has small holes/slits at the circumference, functionally divides the blood volume into small portions (blood films) and reduces the blood thickness layer. The diffusion rate of gas inside the blood medium is inversely proportional to the thickness of the blood layer i.e., thinner blood film results in a better diffusion rate.

For the oxygenation to be effective and the blood not to reach the bottom of the oxygenator quickly, the entire middle chamber rotates as one unit, thus increasing the dwell time of the blood within the rotating chamber. Without rotation the blood is subject to the gravitational force and will reach to the bottom of the oxygenator quickly according to the formula: $t=\sqrt{2h/g}$, where h is the height of the cylinder and g is the gravitational acceleration (assuming no friction with air). By using the centrifugal force, the blood is pressed against the wall of the cylinder and slides until it reaches the bottom. The path of the blood is increased therefore the time the blood is subjected to oxygenation is longer. The centrifugal force is expressed by the formula: $F=mw^2r$, where w is the angular velocity of the rotating cylinder (rad/sec), r is the radius of the rotating cylinder and m is the mass of the blood. Changing the motor RPM affects the value of the centrifugal force.

Upon usage of the novel oxygenator of the invention there is a minimal pressure drop since the blood flows down onto the walls of the rotatable chamber and not through and between fibers. Less resistance to the blood flow, therefore the blood differential pressure ($\Delta P$) is very low. A low pressure drop results in minimal sheer stress. In summary, unlike the commercially available oxygenators which are based on hollow fibers membranes (in which gas flow inside the fibers and the blood flow in between), novel oxygenator is a membrane-less device that allows for direct blood-gas contact which facilitates the required gas exchange, without the need for a separating membrane that affects the blood components.

In some optional embodiments the novel oxygenator may comprise sensors. In some other optional embodiments of the invention, a gas mixer may be used. The gas mixer may flow gases in a precise and controlled manner as required and may interface with the oxygenator's controller and/or with an extracorporeal oxygenation system controller as well as with other various sensors.

Figure 7A:
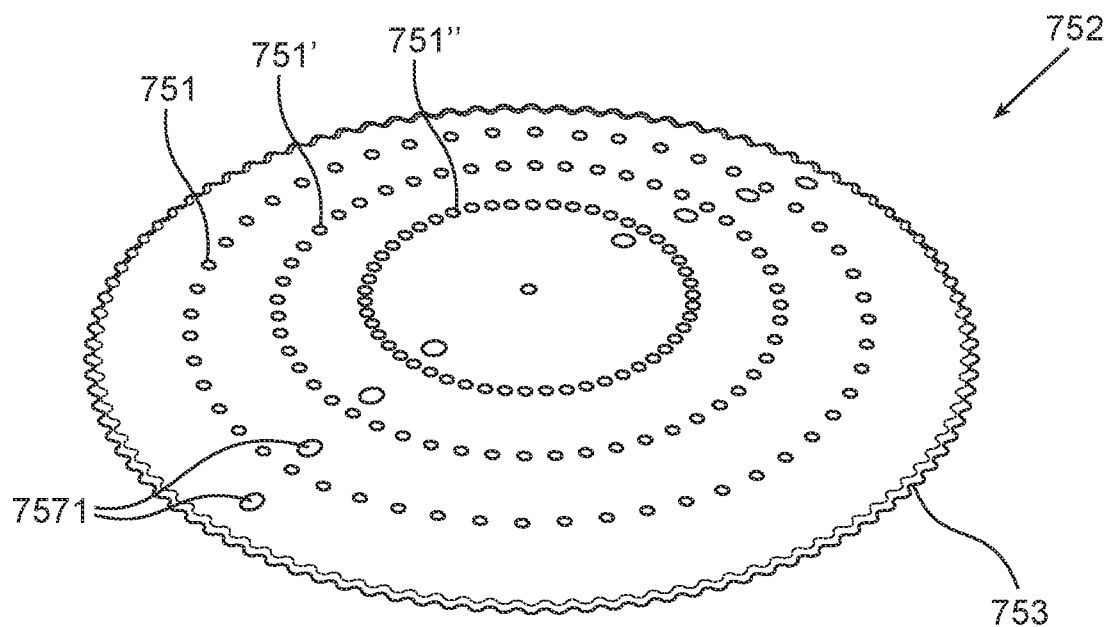
FIG. 7A is a schematic illustration of another optional example of a dome.

FIG. 7A is a schematic illustration of another example of a blood channeling element 752. According to this example, the blood channeling element is also designed as a dome that comprises at least one additional circle of blood entrance holes besides semi-holes 753 at the circumference of dome 752, for increasing the oxygenation rate of the patient's blood. In the specific example described in this drawing, dome 752 comprises additional three "rings" of holes 751, 751', and 751". The blood enters through upper chamber 120 in the same path as described above, however when it falls on top of dome 752 a portion of the blood flow downward through the set of holes comprised in ring 751, other portion of the blood flows through the set of holes comprised in ring 751', and additional portion of the blood flows through the set of holes of ring 751", all in addition to the blood that flows through semi holes 753 at the circumference of dome 752.

Figure 7B:
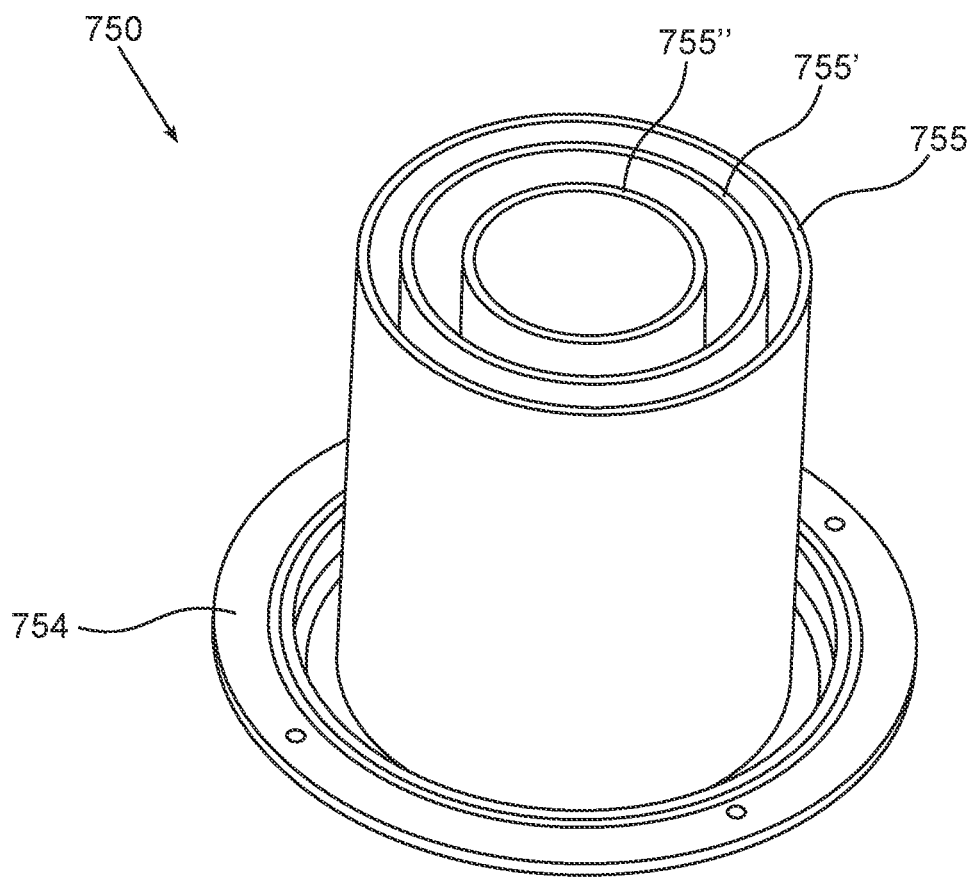
FIG. 7B is an optional middle unit design having inner walls complementary to the holes in the dome of FIG. 7A.
Figure 7C:
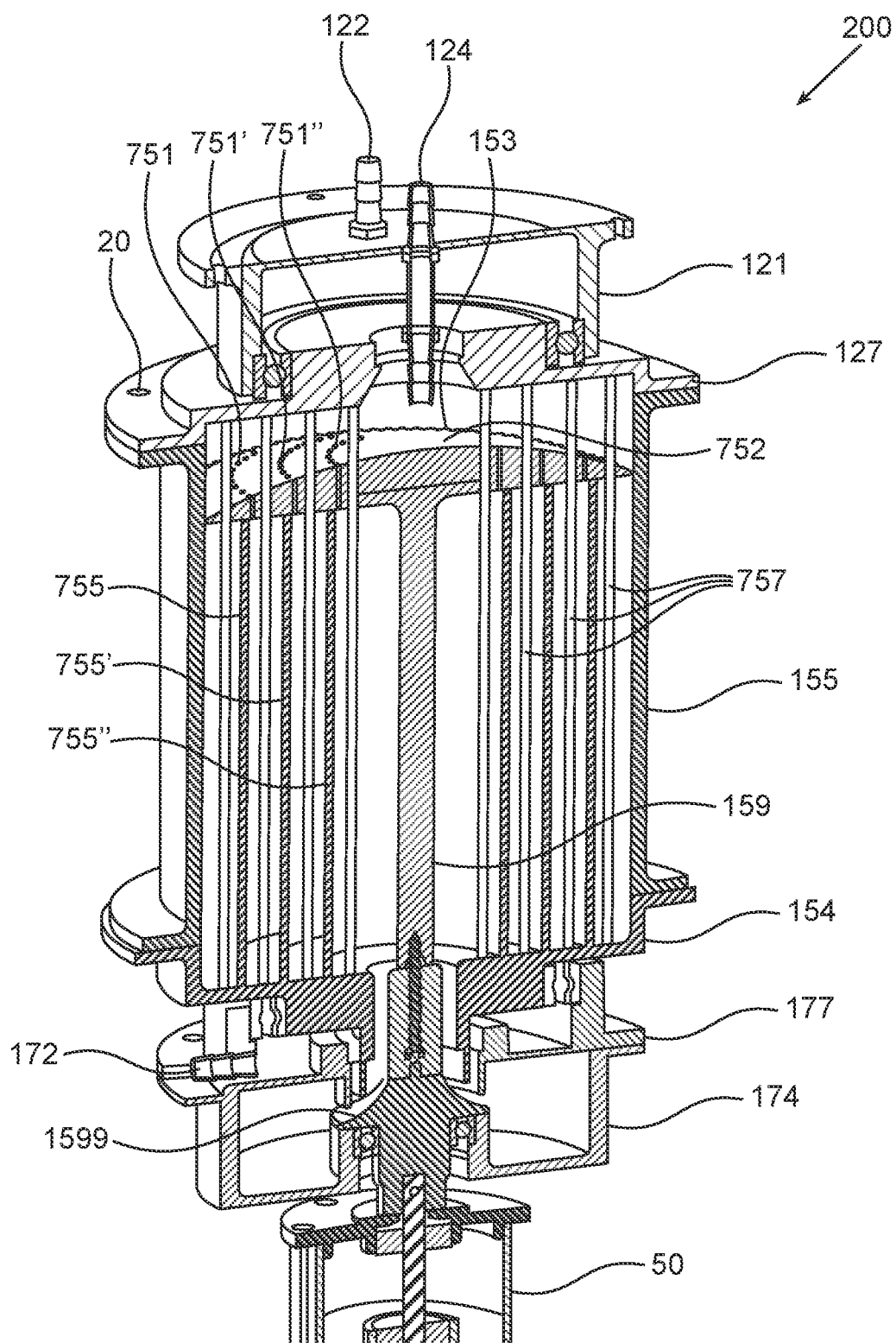
FIG. 7C is a cross section view of an oxygenator comprising the dome and inner walls illustrated in FIGS. 7A-7B in accordance with embodiments of the invention.

FIG. 7B is an optional middle unit design 750 having additional three inner walls each adjacent to specific blood entrance ring of holes of the dome of FIG. 7A. Below each of the rings 751, 751', and 751" there is a complementary wall 755, 755', and 755" respectively that extends from the dome to the floor of the rotatable chamber. The walls are positioned vertically to each set of holes, such that the blood that enters through each ring of holes comes across the wall below it and moves downward on the wall's surface. It should be clear that the embodiment described in FIGS. 7A-7C is only one optional embodiment and the number of rings of holes and complementary walls to each ring may vary and should not be limited to the specific example illustrated herein. The rotation movement of this chamber extends the time duration that it takes the blood to flow from top to bottom (the dwell time) until it reaches the blood drainage holes, and consequently the time for gas exchange, e.g., the time duration that oxygenation of the blood may occur, increases. The multi rings structure increases the total surface area between the oxygen and the deoxidated blood that flows inside the oxygenator and allows to minimize the time required to efficiently oxygenate the patient's blood. The oxygenated blood from all the inner walls passes through the drainage openings at the rotatable chamber floor to the blood collecting unit that gathers all the oxygenated blood to return it back to the patient. The inner walls 755, 755' and 755" practically divide the rotatable chamber 750 into several sub-chambers. In order to allow efficient oxygenation of the patient's blood each circular ring of hole has adjacent to it at least one gas opening and/or a perforated gas column receiving the oxygen through a corresponding hole 7571 at the dome 752.

FIG. 7C is a schematic cross section illustration of an oxygenator 200 comprising the dome 752 and inner walls 755, 755', and 755" as illustrated in FIGS. 7A-7B in accordance with embodiments of the invention. The cross section view allows to see the multiple sub-chambers within the rotatable section of the oxygenator and the multiple gas perforated columns 757 dispersed in each and every sub-chamber created by the inner walls. In the specific example illustrated herein, each sub-chamber contains two gas columns 757, however, the described is a none limiting example and in accordance with this invention each sub chamber may contain one or more gas columns according to a desired design. Blood from the patient enters into oxygenator 200 through blood inlet connector 124 and being poured onto dome 752 that channels the blood to further flow downward at the rotatable chamber through holes 751, 751', 751" and 753. As the blood enters through each ring of holes it is "enforced" to flow on the surface of the corresponding wall until it reaches the bottom. Along this path the blood is rotated and oxygenated, and carbon dioxide diffuses from the blood into the oxygenator and discharges from the oxygenator at the bottom chamber through gas exit pipe 172 to the room. The oxygenated blood is gathered from all chambers at the bottom into blood collecting chamber 174 and delivered back to the patient.

Housing 121 of the first chamber 120 comprises gas inlet connector 122 that flows gas into the space encompasses by housing 121 and enters the gas perforated columns 757 by holes in base 127 (not shown). Also shown in this view are rotatable chamber housing 155, rotation rod 159 connected to floor 154 that connects to a motor 50 through connector 1599, floor 154, base 177, and holes 20.

Figure 8:
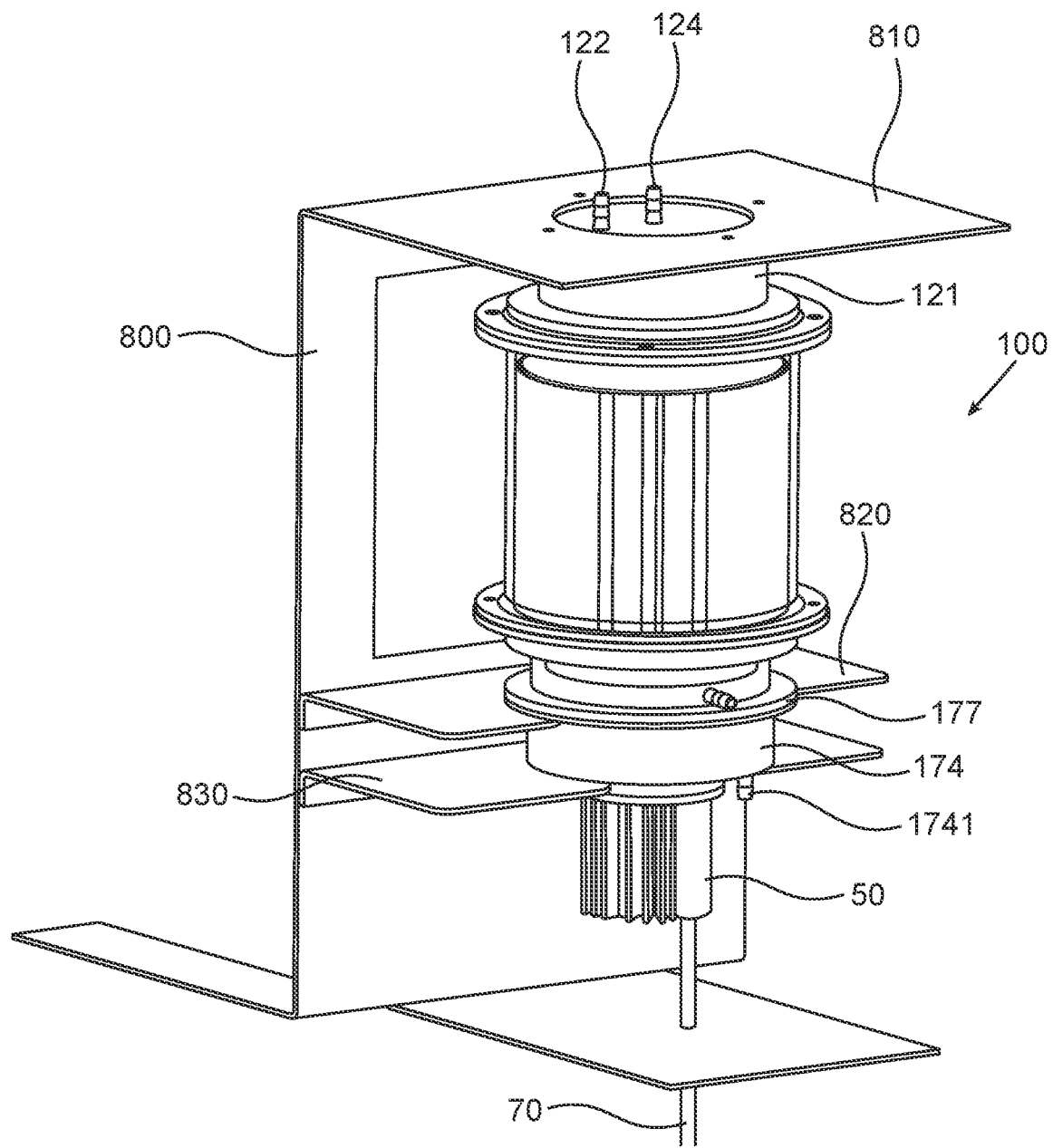
FIG. 8 is a schematic illustration of the oxygenator of FIG. 1A positioned on a dedicated stationary stand that serves as a fixator for the stationary parts of the first and the second chambers of the oxygenator in accordance with optional embodiments of the invention.

FIG. 8 is a schematic illustration of oxygenator 100 of FIG. 1A positioned on a dedicated stand 800 ready to be connected to other components of an extracorporeal life support system, intravascular oxygenation systems, and implanted oxygenating and/or gas exchanging devices.

Stand 800 holds the stationary chambers of oxygenator 100 to stabilize it upon usage and prevent the entire device from rotating. In the specific example illustrated in this drawing stand 800 supports oxygenator 100 in several areas. Plate 810 is connected to housing 121 and support first chamber to remain stationary at the relevant parts, plate 820 connects to both, the blood collecting chamber 174 and base 177, and support second chamber 170 to remain stationary at the relevant parts, and plate 830 connects to motor 50 to stabilize it and prevent it to rotate. Optionally, the motor may be connected to oxygenator 100 via magnetic coupling forces.

In accordance with the embodiment illustrated herein, gas inlet connector 122 is connected by a tube to a gas source. The gas source may be a portable gas balloon, or a stationary gas line port supplied from a wall as usually practiced in medical centers.

Blood inlet connector 124 is connected to a tube that delivered the blood via a cannula from the patient's body using a pump to the oxygenator. The blood from the patient may be delivered first to a storage container before it is delivered to oxygenator 100.

Blood exit connector 1741 is connected to a tube that delivers the oxygenated blood back to the patient's body.

Optionally, motor 50 may be connected by a cable 70 to power source. Alternatively, the motor may be operated by a battery or wirelessly be charged.

It should be clear that the description of the embodiments and attached Figures set forth in this specification serves only for a better understanding of the invention, without limiting its scope. It should also be clear that a person skilled in the art, after reading the present specification could make adjustments or amendments to the attached Figures and above-described embodiments that would still be covered by the present invention.

The invention claimed is:

1. A blood-gas exchange device comprising:
   a. a first chamber comprising at least: a gas inlet and a blood inlet for insertion of blood and gas into the blood-gas exchange device for oxygenating the blood and/or for removing carbon dioxide from the blood;
   b. a second chamber comprising at least: a blood exit for delivering the oxygenated and/or decarbonated blood out from the blood-gas exchange device, and a gas exit configured to allow flow of gases out from the blood-gas exchange device into the surrounding; and
   c. a rotatable chamber connected to said first and second chambers, said rotatable chamber comprising at least:
      a) a blood channeling element configured to direct the inserted blood to flow on the walls of the rotatable chamber through at least one set of opening and/or semi-openings;
      b) at least one gas opening configured to allow flow of the inserted gas from said first chamber into said rotatable chamber toward the flowing blood, and at least one gas opening configure to allow gas flow from the rotatable chamber to the second chamber; and
      c) a motor configured to spin said rotatable chamber;
   wherein, the circular movement of the rotatable chamber channels the blood to flow along the rotatable chamber walls, forming a blood layer on the wall that directly contacts with the gas and allows gas exchange.

2. The blood-gas exchange device according to claim 1, wherein said blood is inserted into the blood-gas exchange device from said blood inlet and returned to said blood exit upon oxygenation and/or removal of carbon dioxide.

3. The blood-gas exchange device according to claim 2, wherein said blood inlet and blood exit, each is connected to a tube that delivers blood from a blood source and/or a storage container into the blood-gas exchange device and return the blood following the gas exchange to the blood exit.

4. The blood-gas exchange device according to claim 3, further comprising at least one pump configured to withdraw blood from said blood source or from the storage container into the blood-gas exchange device and to transfer the oxygenated/decarbonated blood back to the blood exit.

5. The blood-gas exchange device according to claim 1, wherein said blood is inserted into the blood-gas exchange device via said blood inlet from a blood storage container and returned to said blood exit after oxygenation and/or removal of carbon dioxide.

6. The blood-gas exchange device according to claim 1, wherein said gas inlet and gas exit are both positioned in one chamber, and wherein said at least one gas opening configured to allow gas flow into and from said rotatable chamber is comprised in the chamber that comprise the gas inlet and the gas exit.

7. The blood-gas exchange device according to claim 1, wherein said blood layer is either one of a blood channel or a blood film formed by the division of the inserted blood by the blood channeling element into plurality of smaller portions and the circular movement of the rotatable chamber.

8. The blood-gas exchange device according to claim 1, wherein said blood channeling element is a convex surface having at least one set of openings or partial openings at its circumference.

9. The blood-gas exchange device according to claim 1, wherein said at least one set of openings or partial openings, is adjacent to the rotatable chamber wall such that the blood that flows through the set of openings or partial openings is forced to flow downward on said wall until it reaches the second chamber.

10. The blood-gas exchange device according to claim 1, wherein said blood channeling element comprises at least two sets of openings/partial openings, each set of opening is adjacent to a wall such that the inserted blood flows within the rotatable chamber on each of said adjacent walls until it reaches the second chamber.

11. The blood-gas exchange device according to claim 1, wherein said gas opening is configured to insert into the blood-gas exchange device either one of the following gases: pure oxygen, air, enriched air with oxygen at various ratios, nitrogen, carbon dioxide and mixture thereof.

12. The blood-gas exchange device according to claim 1, further comprising at least one perforated gas column configured to connect between one gas opening at the first chamber and one gas opening at the second chamber, said at least one perforated gas column is crossing through said rotatable chamber and allows flow of gas from the column toward the flowing blood and vice versa.

13. The blood-gas exchange device according to claim 1, wherein said gas exchange is either oxygenation of the blood or decarbonation of the blood or a combination thereof.

14. The blood-gas exchange device according to claim 1, wherein the dwell time for gas exchange is elongated by the circular movement of the rotatable chamber.

15. The blood-gas exchange device according to claim 1, wherein said flow of gas through the gas inlet and exit of gas through the gas exit is continuous and allows a gradient flow of gases within the blood-gas exchange device that enables gases from the blood to diffuse into the rotatable chamber and gases from the rotatable chamber to diffuse into the flowing blood.

16. A blood-gas exchange device according to claim 1, wherein instead of blood another body fluid is inserted for gas exchange procedure.

\* \* \* \* \*

UNITED STATES PATENT AND TRADEMARK OFFICE
CERTIFICATE OF CORRECTION

| | | |
|---|---|---|
| PATENT NO. | : 11,938,257 B1 | |
| APPLICATION NO. | : 18/235515 | |
| DATED | : March 26, 2024 | |
| INVENTOR(S) | : Aviran Sender and Angelina Rozentsveig | |

It is certified that error appears in the above-identified patent and that said Letters Patent is hereby corrected as shown below:

On the Title Page

(72) Inventors should read: Aviran Sender, Haifa (IL); Angelina Rozentsveig, Tel aviv (IL)

Signed and Sealed this
Eighth Day of October, 2024

Katherine Kelly Vidal
*Director of the United States Patent and Trademark Office*